US00PP17959P2

(12) United States Plant Patent
Danziger

(10) Patent No.: US PP17,959 P2
(45) Date of Patent: Aug. 28, 2007

(54) ***SUTERA* PLANT NAMED 'DANOVA912'**

(50) Latin Name: *Sutera hybrida*
Varietal Denomination: Danova912

(75) Inventor: Gabriel Danziger, Beit Dagan (IL)

(73) Assignee: Danziger "Dan" Flower Farm, Post Beit Dagan, IL (US)

( * ) Notice: Subject to any disclaimer, the term of this patent is extended or adjusted under 35 U.S.C. 154(b) by 0 days.

(21) Appl. No.: 11/349,668

(22) Filed: Feb. 7, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—C. A. Whealy

(57) ABSTRACT

A new and distinct cultivar of *Sutera* plant named 'Danova912', characterized by its outwardly spreading and low mounding plant habit; vigorous growth habit; freely branching habit; early and continuous flowering habit; large light pink-colored flowers with darker pink-colored centers; and good garden performance.

1 Drawing Sheet

Botanical designation: *Sutera hybrida.*
Cultivar denomination: 'DANOVA912'.

BACKGROUND OF THE INVENTION

The present Invention relates to a new and distinct cultivar of *Sutera* plant, botanically known as *Sutera hybrida,* and hereinafter referred to by the cultivar name 'Danova912'.

The new *Sutera* is a product of a planned breeding program conducted in Moshav Mishmar Hashiva, Israel. The objective of the breeding program is to develop new uniform *Sutera* cultivars with large and numerous flowers.

The new *Sutera* originated from an open-pollination in August, 2002 of a proprietary selection of *Sutera hybrida* identified as code number BA-2-21, not patented, as the female, or seed, parent with an unidentified selection of *Sutera hybrida,* as the male, or pollen, parent. The cultivar Danova912 was discovered and selected by the Inventor as a flowering plant within the progeny from the aforementioned open-pollination in a controlled environment in Moshav Mishmar Hashiva, Israel in March, 2003.

Asexual reproduction of the new cultivar by terminal cuttings in Moshav Mishmar Hashiva, Israel since March, 2003, has shown that the unique features of this new *Sutera* are stable and reproduced true to type in successive generations.

SUMMARY OF THE INVENTION

Plants of the cultivar Danova912 have not been observed under all possible environmental conditions. The phenotype may vary somewhat with variations in environment such as temperature and light intensity without, however, any variance in genotype.

The following traits have been repeatedly observed and are determined to be the unique characteristics of 'Danova912'. These characteristics in combination distinguish 'Danova912' as a new and distinct cultivar of *Sutera:*

1. Outwardly spreading and low mounding plant habit.

2. Vigorous growth habit.
3. Freely branching habit.
4. Early and continuous flowering habit.
5. Large light pink-colored flowers with darker pink-colored centers.
6. Good garden performance.

Compared to plants of the female parent selection, plants of the new *Sutera* flower earlier and have larger flowers. In addition, plants of the new *Sutera* and the female parent selection differ in flower color as plants of the female parent selection have lavender-colored flowers.

Plants of the new *Sutera* can be compared to plants of the *Sutera hispida* cultivar Dancoplace, disclosed in U.S. Plant Pat. No. 14,458. In side-by-side comparisons, plants of the new *Sutera* differed from plants of the cultivar Dancoplace in the following characteristics:

1. Plants of the new *Sutera* flowered earlier than plants of the cultivar Dancoplace.
2. Plants of the new *Sutera* had larger flowers than plants of the cultivar Dancoplace.
3. Plants of the new *Sutera* and the cultivar Dancoplace differed in flower color as plants of the cultivar Dancoplace had white-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the colors of the new *Sutera.*

The photograph at the bottom of the sheet comprises a side perspective view of a typical flowering plant of 'Danova912' grown in a container.

The photograph at the top of the sheet comprises a close-up view of typical flowers and leaves of 'Danova912'.

DETAILED BOTANICAL DESCRIPTION

The aforementioned photographs and following observations and measurements describe plants grown in Bonsall, Calif., in an outdoor nursery during the winter with day temperatures ranging from 18° C. to 35° C. and night temperatures ranging from 10° C. to 18° C. Plants were grown in 15-cm containers and were about three months old. Color references are made to The Royal Horticultural Society Colour Chart, 1995 Edition, except where general terms of ordinary dictionary significance are used.

Botanical classification: *Sutera hybrida* cultivar Danova912.

Parentage:

*Female, or seed, parent.*—Proprietary selection of *Sutera hybrida* identified as code number BA-2-21, not patented.

*Male, or pollen, parent.*—An unidentified selection of *Sutera hybrida,* not patented.

Propagation:

*Type cutting.*—Terminal vegetative cuttings.

*Time to initiate roots, summer.*—About seven days at 24° C.

*Time to initiate roots, winter.*—About ten days at 18° C.

*Time to produce a rooted young plant, summer.*—About 15 days at 24° C.

*Time to produce a rooted young plant, winter.*—About 18 days at 18° C.

*Root description.*—Fine, fibrous; white in color.

*Rooting habit.*—Freely branching; dense.

Plant description:

*Form.*—Outwardly spreading and low mounding plant habit. Freely and continuously branching with about six primary lateral branches each with about four to six secondary lateral branches. Vigorous growth habit.

*Plant height.*—About 10 cm.

*Plant diameter.*—About 45 cm.

*Lateral branches.*—Length: About 25 cm. Diameter: About 2 mm. Internode length: About 2.4 cm. Texture: Pubescent; minute. Strength: Strong. Color: 146B.

*Foliage description.*—Arrangement: Opposite; simple. Length: About 1.1 cm. Width: About 1.5 cm. Shape: Broadly elliptic to nearly oval. Apex: Broadly acute. Base: Acute. Margin: Shallow serrations. Texture, upper and lower surfaces: Sparsely pubescent. Venation pattern: Pinnate, arcuate. Color: Developing foliage, upper surface: 146A. Developing foliage, lower surface: 146B. Fully expanded foliage, upper surface: 147A; venation, 147A. Fully expanded foliage, lower surface: 147B; venation, 147B. Petiole length: About 4 mm. Petiole diameter: About 2 mm. Petiole texture, upper and lower surfaces: Sparsely pubescent. Petiole color, upper and lower surfaces: 147B.

Flower description:

*Flower type and habit.*—Solitary axillary flowers; salverform; slender corolla tubes flare abruptly into five rounded lobes. Flowers persistent. Very freely flowering; typically about 52 flower buds and open flowers per lateral branch. Flowers face mostly upward or outward. Flowers persistent.

*Natural flowering season.*—Plants typically flower from spring until fall; flowering continuous during this period.

*Flower longevity on the plant.*—About five to six days.

*Fragrance.*—None detected.

*Flower diameter.*—About 1.6 cm.

*Flower depth.*—About 8 mm.

*Flower buds.*—Length: About 7 mm. Diameter: About 3 mm. Shape: Obovate. Color: Fainter than 65D.

*Corolla.*—Quantity/arrangement: Five fused petals; slender corolla tube flaring abruptly into five rounded lobes. Petal lobe length from throat: About 6 mm. Petal lobe width: About 6 mm. Petal lobe shape: Roughly spatulate. Petal lobe apex: Rounded. Petal lobe margin: Entire. Texture, upper and lower surfaces: Smooth, glabrous. Color: When opening, upper and lower surfaces: Close to 155D. Fully opened, upper surface: Close to 56D; towards the base, 75B; color becoming closer to 155D with development. Fully opened, lower surface: 56D. Flower throat (inside): 21A. Flower tube (outside): 15D.

*Sepals.*—Arrangement/appearance: Single whorl of five sepals fused at base; star-shaped calyx. Length: About 5 mm. Width: Less than 1 mm. Shape: Lanceolate. Apex: Acute. Margin: Entire. Texture, upper and lower surfaces: Pubescent, minute. Color, upper and lower surfaces: 146B.

*Peduncles.*—Length: About 1 cm. Width: Less than 1 mm. Angle: About 45° from the stem. Strength: Strong. Texture: Pubescent; minute. Color: 146C.

*Reproductive organs.*—Stamens: Quantity per flower: Four. Anther shape: Oval. Anther length: About 1 mm. Anther color: 14A. Pollen amount: Scarce. Pollen color: 14A. Pistils: Quantity per flower: One. Pistil length: About 1 cm. Style length: About 8 mm. Style color: 145B. Stigma shape: Round. Stigma color: 146A. Ovary color: 145A.

*Seed/fruit.*—Seed and fruit production has not been observed.

Disease/pest resistance: Plants of the new *Sutera* have not been noted to be resistant to pathogens or pests common to *Sutera.*

Garden performance: Plants of the new *Sutera* have been observed to have good garden performance. Plants of the new *Sutera* tolerate temperatures from about 2° C. to 38° C. and to tolerate wind and rain.

It is claimed:

1. A new and distinct cultivar of *Sutera* plant named 'Danova912', as illustrated and described.

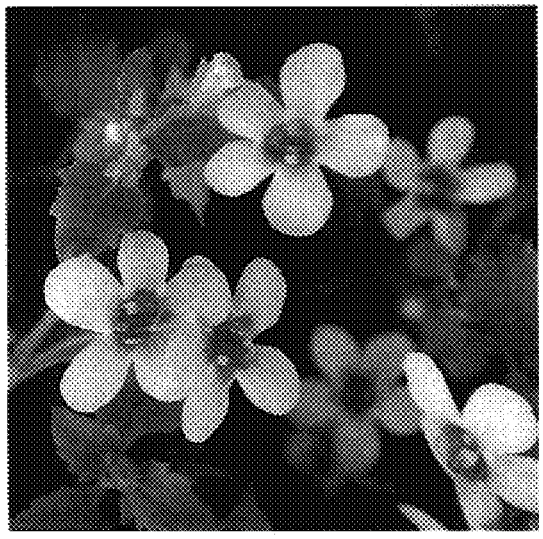
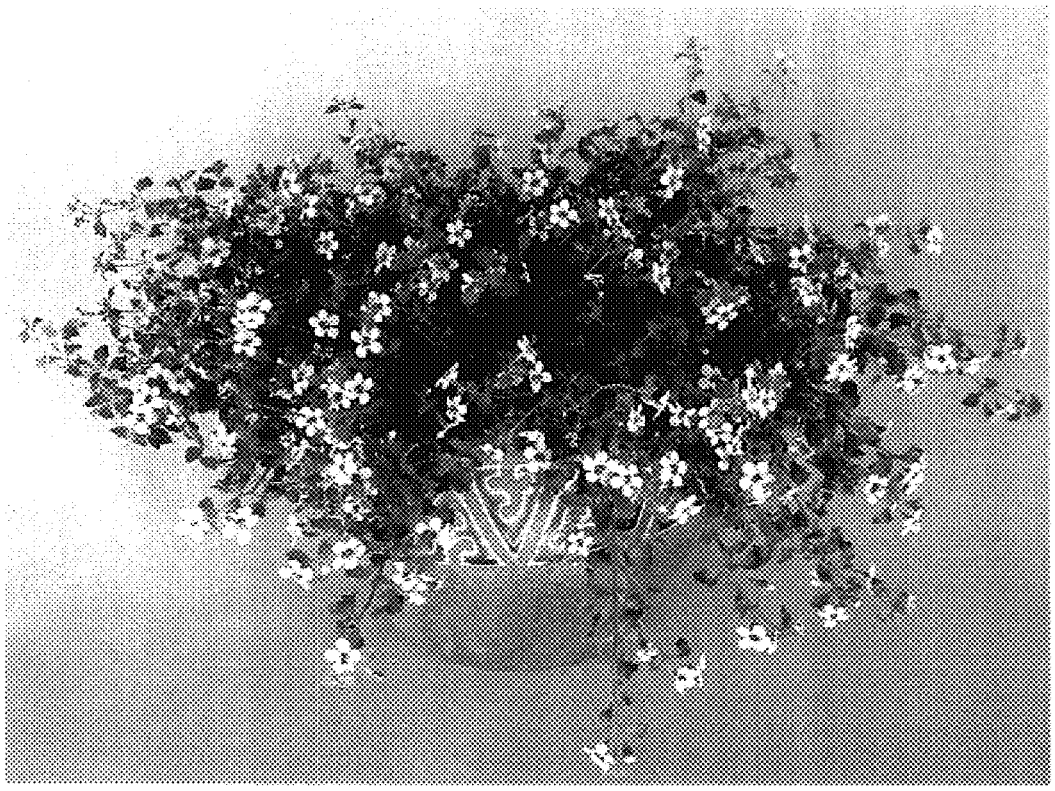

* * * * *